United States Patent
Mostoller

(10) Patent No.: US 7,354,888 B2
(45) Date of Patent: Apr. 8, 2008

(54) ANTIBACTERIAL COMPOSITION AND METHODS THEREOF COMPRISING A TERNARY BUILDER MIXTURE

(75) Inventor: Charles R. Mostoller, Langhorne, PA (US)

(73) Assignee: Danisco A/S (DK)

( * ) Notice: Subject to any disclaimer, the term of this patent is extended or adjusted under 35 U.S.C. 154(b) by 0 days.

(21) Appl. No.: 10/985,610

(22) Filed: Nov. 10, 2004

(65) Prior Publication Data

US 2006/0100124 A1    May 11, 2006

(51) Int. Cl.
C11D 7/14    (2006.01)
C11D 7/16    (2006.01)
C11D 7/10    (2006.01)

(52) U.S. Cl. .............. 510/111; 510/511; 510/512; 510/531; 510/533; 510/534; 510/361; 510/398; 510/434; 510/477; 510/486

(58) Field of Classification Search .............. 510/111, 510/511, 512, 531, 533, 534, 361, 398, 434, 510/477, 486

See application file for complete search history.

(56) References Cited

U.S. PATENT DOCUMENTS

| | | | |
|---|---|---|---|
| 3,852,220 A * | 12/1974 | Kimmel et al. ............. 510/461 |
| 3,934,044 A | 1/1976 | Busch et al. | |
| 3,958,026 A | 5/1976 | Leone et al. | |
| 3,996,386 A | 12/1976 | Malkki et al. | |
| 4,044,160 A | 8/1977 | Erickson et al. | |
| 4,062,982 A | 12/1977 | McMillan et al. | |
| 4,075,357 A | 2/1978 | Szczesniak et al. | |
| 4,122,187 A | 10/1978 | Kotani et al. | |
| 4,247,569 A | 1/1981 | Hata et al. | |
| 4,348,419 A | 9/1982 | Thompson et al. | |
| 4,362,753 A | 12/1982 | Barta | |
| 4,400,403 A | 8/1983 | Robach | |
| 4,431,679 A | 2/1984 | Crawford | |
| 4,515,789 A | 5/1985 | Metzger et al. | |
| 4,740,593 A | 4/1988 | Gonzalez et al. | |
| 4,762,822 A | 8/1988 | Ettinger | |
| 4,766,646 A | 8/1988 | Parker | |
| 4,808,330 A | 2/1989 | Chung | |
| 4,897,220 A * | 1/1990 | Trieselt et al. .............. 510/360 |
| 4,931,102 A * | 6/1990 | Burke ........................... 134/2 |
| 5,069,992 A | 12/1991 | Tachikawa et al. | |
| 5,096,718 A | 3/1992 | Ayres et al. | |
| 5,204,060 A | 4/1993 | Allenmark et al. | |
| 5,277,823 A | 1/1994 | Hann et al. | |
| 5,283,073 A | 2/1994 | Bender et al. | |
| 5,302,406 A | 4/1994 | Ludwig et al. | |
| 5,366,509 A * | 11/1994 | Ota et al. ...................... 8/108.1 |
| 5,389,390 A | 2/1995 | Kross | |
| 5,436,017 A | 7/1995 | Ludwig et al. | |
| 5,549,895 A | 8/1996 | Lyon et al. | |
| 5,629,282 A | 5/1997 | Bhakoo | |
| 5,763,384 A * | 6/1998 | Ormerod, IV .............. 510/380 |
| 6,010,729 A | 1/2000 | Gutzmann et al. | |
| 6,033,705 A | 3/2000 | Isaacs | |
| 6,103,286 A | 8/2000 | Gutzmann et al. | |
| 6,123,981 A | 9/2000 | Bender et al. | |
| 6,207,210 B1 | 3/2001 | Bender et al. | |
| 6,210,678 B1 | 4/2001 | Richards | |
| 6,287,617 B1 | 9/2001 | Bender et al. | |
| 6,329,011 B1 | 12/2001 | Oita | |
| 6,352,727 B1 | 3/2002 | Takahashi | |
| 6,372,710 B2 * | 4/2002 | Sadoyama .................. 510/531 |
| 6,395,185 B1 * | 5/2002 | Gauthier et al. ............. 210/701 |
| 6,432,892 B2 * | 8/2002 | Meine et al. ................ 510/111 |
| 6,451,365 B1 | 9/2002 | King et al. | |
| 6,534,075 B1 | 3/2003 | Hei et al. | |
| 6,620,446 B2 | 9/2003 | King et al. | |
| 6,740,628 B2 * | 5/2004 | Bennie et al. .............. 510/221 |
| 2003/0194475 A1 | 10/2003 | Bender et al. | |
| 2004/0097390 A1 * | 5/2004 | Jordan et al. ............... 510/189 |

FOREIGN PATENT DOCUMENTS

| | | |
|---|---|---|
| EP | 0 659 346 A1 | 6/1995 |
| FR | 2860998 | 4/2005 |
| GB | 2009222 | 6/1979 |
| WO | WO 89/00194 | 1/1989 |
| WO | WO 97/23136 | 7/1997 |
| WO | WO 00/18888 | 4/2000 |
| WO | WO 03/003842 | 1/2003 |
| WO | WO 2004/057984 | 7/2004 |
| WO | WO 2004/078662 | 9/2004 |
| WO | WO 2005/123147 | 12/2005 |

* cited by examiner

Primary Examiner—Charles Boyer
(74) Attorney, Agent, or Firm—Fay Sharpe LLP

(57) ABSTRACT

Provided is an antibacterial aqueous solution comprising a phosphate, a citrate, and a silicate; a method of controlling bacterial contamination and/or growth in food substance; a method of prohibiting the formation of, and/or facilitating the removing of, silicate aggregation on metal article; and a method of reducing phosphate usage in industrial antibacterial process.

41 Claims, No Drawings

ANTIBACTERIAL COMPOSITION AND METHODS THEREOF COMPRISING A TERNARY BUILDER MIXTURE

BACKGROUND OF THE INVENTION

The present invention relates to an antibacterial aqueous solution comprising a phosphate, a citrate, and a silicate. The present invention is also related to a method of controlling bacterial contamination and/or growth in a food substance, a method of prohibiting the formation of, and/or facilitating the removal of, silicate aggregation on a metal substrate, and a method of, for environmental protection purposes, reducing phosphate usage in industrial antibacterial processes.

Bacteria live everywhere in our environment, air, soil, rock, and water. Many bacteria are pathogenic and can cause diseases such as Botulism food poisoning, *E-coli* food poisoning, Cholera, Whooping Cough, Plague, Scarlet fever, Diphtheria, Tuberculosis, Typhoid fever, Anthrax, and so on and so forth. The extent of food borne infections in the United States was quantitatively documented in the CAST report of 1994 (Foodborne Pathogens: Risks and Consequences. Task Force Report No. 122, Council for agricultural Science and Technology, Washington D.C.), and has been extensively characterized in the past few years (CDC. 1988c. 1997 Final FoodNet Surveillance report. U.S. Department of Health and Human Services, October, 1998). Many other bacteria are, although not pathogens, spoilage bacteria and are responsible for reducing the shelf life and freshness of a food substance.

Without appropriate sanitary measures, human food substances such as fruit, vegetable, and animal meat will inevitably be contaminated or degraded by bacteria. For example, the so-called "salad in a bag" products have gained great consumer acceptance as a result of their convenience of use. However, such products are susceptible to bacterial degradation as a result of cross contamination of bacteria at the surface of one or more cut pieces of vegetables contacting other cut pieces. Similarly, animals are killed and their carcasses are processed to produce food products for human consumption. Typically, the processing of such animals includes evisceration, which may contaminate the edible portion of the animal with bacteria. Furthermore, depending upon the sanitary conditions employed in processing, additional sources for contamination exist.

Moreover, poultry carry a large population of microbes on their surface as they pass into a scalder, a typical early stage processing technique. Microbes are displaced into the scald water and can redeposit on the bird as it is removed therefrom. In addition, poultry feces may be ejected into the scald water which further escalates the presence of microbes therein. Scalded birds are then defeathered in mechanical pickers, which are often set so that the skin's epidermal layer is removed. This allows microbes to more easily bind to the naked bird. Beef carcasses similarly carry microbes on their hide into a slaughter room. Because of the violent nature of hide removal, microbe containing debris can be air-born and land on the naked carcass. Unfortunately, removal of microbes from the naked carcass of poultry or beef is difficult. Accordingly, methods of removing these microbes have been investigated.

There has been extensive research conducted in the field of food hygiene to develop compositions which function as food grade anti-bacterial agents. For example, U.S. Pat. No. 5,436,017 teaches a method of inhibiting bacterial growth in meat in which sodium citrate buffered with citric acid is introduced into the meat to a sodium citrate content of 1 to 7%, and preferably about 1 to 1.3%.

WO 97/23136 teaches a bacterial decontamination method which involves treatment with a solution of low concentration alkali metal orthophosphate combined with either osmotic shock and/or lysozyme in solution and/or nisin in solution. This reference tested the combination of low concentrations of trisodium orthophosphate with lysozyme against certain bacteria on lettuce leaves or chicken skin, and the combination of low concentrations of trisodium orthophosphate with nisin against certain bacteria on chicken skin. U.S. Pat. No. 5,283,073 has disclosed a process for treating poultry carcasses with a solution containing about 4% or greater trialkali metal phosphate, to remove, reduce or retard bacterial contamination and/or growth. However, according to the disclosure, relatively undesirable high amounts of phosphates will be dumped into waste streams and eventually into the environment. Phosphates are a major source of pollution in lakes and streams, and high phosphate levels support over-production of algae and water weeds.

In an attempt to minimize, or hopefully eliminate, the use of phosphates, U.S. Patent Application 2003/0,194,475 teaches an antibacterial method for food substances, in which a phosphate solution is replaced by an aqueous solution of alkali silicate. However, silicate tends to "aggregate" into an insoluble form and binds very tightly on the surface of metal, particularly iron based metals, such as shackles and drip pans. This aggregated silicate may commonly appear as "scale", white spot, stain, or gummy residue, all of which are difficult to remove. For purposes of this disclosure, each of these is referred to generally as scale. Scale is generally perceived as undesirable as it may provide a surface prone to bacteria/microbe infiltration.

Advantageously, the present invention provides an antibacterial aqueous solution, which can reduce certain of the aforementioned problems. More particularly, the present invention can reduce bacterial contamination and/or retard bacterial growth in a food substance; yield a waste stream containing a limited amount of phosphate compounds; and limit the formation of, and/or facilitate the removal of, silicate aggregation on metal article.

BRIEF DESCRIPTION OF THE INVENTION

One aspect of the present provides an antibacterial aqueous solution comprising (A) a phosphate having the formula (I), (B) a citrate having the formula (II),

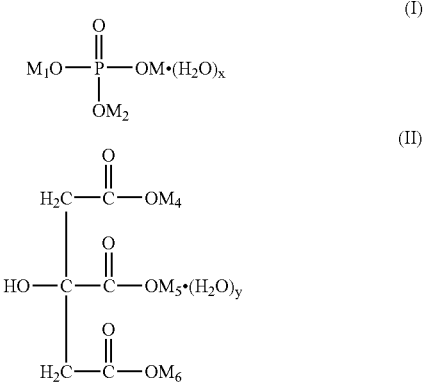

and (C) a silicate having the formula $[(M_7)_2O]\cdot(SiO_2)_m\cdot(H_2O)_z$, in which $M_1$, $M_2$, $M_3$, $M_4$, $M_5$, $M_6$, and $M_7$ are independently of each other selected from the group consisting of Hydrogen, Sodium, and Potassium; x, y, and z are independently of each other any number between 0 and 12; and m is any number between 1 and 6.

Another aspect of the invention provides a method of controlling bacterial contamination and/or growth in food substances, comprising contacting the food substance with a sufficient amount of the above antibacterial solution.

Still another aspect of the invention provides a method of prohibiting the formation of, and/or facilitating the removal of, silicate aggregation on a metal substrate, comprising using the silicate solution as defined above with the metal article.

A further aspect of the invention provides, for environmental reason, a method of reducing phosphate usage in an antibacterial process, comprising using the aqueous solution as defined above instead of a solution containing a higher level of phosphate.

DETAILED DESCRIPTION OF THE INVENTION

Generally, the invention is related to an antibacterial aqueous solution comprising a phosphate, a citrate, and a silicate; a method of controlling bacterial contamination and/or growth in food substances; and a method of prohibiting the formation of, and/or facilitating the removal of, silicate aggregation on a metal substrate.

The antibacterial aqueous solution of the present invention comprises:

(A) a phosphate having the formula (I),

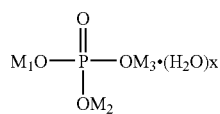
(I)

(B) a citrate having the formula (II),

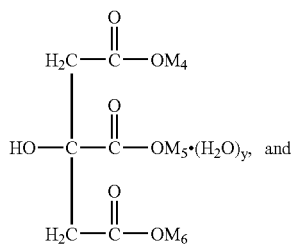
(II)

(C) a silicate having the formula $[(M_7)_2O]\cdot(SiO_2)_m\cdot(H_2O)_z$, in which $M_1$, $M_2$, $M_3$, $M_4$, $M_5$, $M_6$, and $M_7$ are independently of each other selected from the group consisting of Hydrogen, Sodium, and Potassium; x, y, and z are independently of each other any number between 0 to 12; and m is any number between 1 to 6.

As known to a person skilled in the art, when all of $M_1$, $M_2$, and $M_3$ are not hydrogen, the formula (I) phosphate is called phosphate or ortho-phosphate, such as tri-sodium phosphate, tri-sodium phosphate dodecahydrate ($Na_3PO_4\cdot12H_2O$), tri-sodium phosphate hexahydrate, tri-potassium phosphate, and the like. When one of $M_1$, $M_2$, and $M_3$ is hydrogen, the formula (I) phosphate may be called, for example, disodium hydrogenphosphate, sodium hydrogenphosphate, sodium hydrogenphosphate heptahydrate, sec-sodium phosphate, sodium phosphate dibasic, or disodium phosphate, and dipotassium hydrogenphosphate, dipotassium hydrogen phosphate trihydrate, potassium hydrogenphosphate, potassium hydrogenphosphate trihydrate, sec-potassium phosphate, potassium phosphate dibasic, potassium phosphate dibasic trihydrate, dipotassium phosphate, and the like. When two of $M_1$, $M_2$, and $M_3$ are hydrogen, the formula (I) phosphate may be called, for example, sodium dihydrogenphosphate, sodium phosphate monobasic, sodium phosphate monobasic dihydrate, monosodium phosphate, potassium dihydrogenphosphate, potassium phosphate monobasic, monopotassium phosphate, and the like. When all three of $M_1$, $M_2$, and $M_3$ are hydrogen, the formula (I) phosphate becomes phosphoric acid or orthophosphoric acid. In a preferred embodiment of the present invention, $M_1$, $M_2$, and $M_3$ are all sodium and x=12, i.e., tri-sodium phosphate (TSP) dodecahydrate ($Na_3PO_4\cdot12H_2O$).

Although potentially less suitable for the present invention, other phosphor-containing salts or acids may be used singly or in combination with the formula (I) phosphate, for example, metaphosphate ($MPO_3$), phosphite ($M_3PO_3$), metaphosphite ($MPO_2$), pyrophosphate ($M_4P_2O_7$), pyrophosphite ($M_4P_2O_5$), hypophosphite ($M_3PO_2$), peroxy (mono) phosphate ($M_3PO_5$), hypophosphate ($M_4P_2O_6$), hydrated form thereof, and mixture thereof. The definition of the "M" here should be, Mutatis Mutandis, similar to that of the formula (I) phosphate.

Commercially available phosphates of formula (I) include AvGard™ TSP dodecahydrate (Rhodia).

The concentration of the formula (I) phosphate in the antibacterial solution may be in a range of from about 0.1 wt % to about 4 wt %. Preferably, the concentration of the formula (I) phosphate is from about 0.5 wt % to about 2 wt %. In a preferred embodiment, the concentration of the phosphate is about 1 wt % in the antibacterial aqueous solution. The concentrations of the formula (I) phosphate are calculated on the basis of the weight of anhydrous form and the total weight of the antibacterial solution. Either the anhydrous form or a hydrated form of the formula (I) phosphate may be used to form the antibacterial solution, provided that the appropriate adjustment is made to compensate for the weight of any associated water of hydration.

When $M_4$, $M_5$, and $M_6$ are not hydrogen, the formula (II) citrate may be called, for example, sodium citrate, sodium citrate tribasic, citric acid trisodium salt, trisodium citrate, sodium citrate dihydrate, sodium citrate tribasic dihydrate, citric acid trisodium salt dihydrate, trisodium citrate dihydrate, potassium citrate, tripotassium citrate, potassium citrate tribasic, citric acid tripotassium salt, potassium citrate monohydrate, tripotassium citrate monohydrate, potassium citrate tribasic monohydrate, citric acid tripotassium salt monohydrate, and the like. When one of $M_4$, $M_5$, and $M_6$ is hydrogen, the formula (II) citrate may be called, for example, citric acid disodium salt, citric acid disodium salt sesquihydrate (1.5$H_2O$), sodium hydrogencitrate, sodium hydrogencitrate sesquihydrate, disodium hydrogen citrate, disodium hydrogen citrate sesquihydrate, sodium citrate dibasic, sodium citrate dibasic sesquihydrate, and the like. When two of $M_4$, $M_5$, and $M_6$ are hydrogen, the formula (II) citrate may be called, for example, potassium citrate monobasic, potassium dihydrogen citrate, citric acid monopotassium salt, sodium citrate monobasic, sodium dihydrogen citrate, citric acid monosodium salt, and the like. When all three of $M_4$, $M_5$, and $M_6$ are hydrogen, the formula (II) citrate becomes citric acid, citric acid monohydrate, and the like. In a preferred embodiment of the present invention, $M_4$, $M_5$, and $M_6$ are all sodium.

Commercially available citrates of formula (II) include food grade compounds available from Danisco.

The concentration of the formula (II) citrate in the antibacterial aqueous solution may be in a range of from about 0.1 wt % to about 4 wt %. Preferably, the concentration of the formula (II) citrate is from about 0.5 wt % to about 2 wt %. In a preferred embodiment, the concentration of the citrate is about 1 wt % in the antibacterial solution. The concentrations of the formula (II) citrate are calculated on the basis of the weight of anhydrous form and the total weight of the antibacterial solution. Either the anhydrous form or a hydrated form of the formula (II) citrate may be used to form the antibacterial solution, provided that the appropriate adjustment is made to compensate for the weight of any associated water of hydration.

Suitable silicates for the present invention may be anhydrous or hydrated, crystalline or amorphous. Preferred examples of the silicate compounds include, but are not limited to, sodium disilicates, sodium metasilicates, potassium disilicates, potassium metasilicates. More preferred examples comprise anhydrous sodium metasilicate, anhydrous potassium metasilicate, sodium metasilicate pentahydrate, potassium metasilicate pentahydrate, sodium metasilicate hexahydrate, potassium metasilicate hexahydrate, sodium metasilicate nonahydrate, potassium metasilicate nonahydrate, and mixture thereof. In a preferred embodiment, the silicate is a crystalline $[Na_2O].(SiO_2)_m.(H_2O)_z$, in which m may be in the range of 0.5 to 3.5 such as m=1; z may preferably be such that makes the water content of the silicate compound in the range of 0% to 55%, for example z may be in the range from 0 to 9 such as 0, 5, 6, or 9.

Commercially available silicates of formula (II) include those compounds available from PQ Corporation, PA; INEOS, IL; and Oxidental Chemicals, TX.

According to the present invention, the concentration of the silicate may be greater than or equal to 0.05 wt %, for example, from 0.1 wt % to saturation of the silicate in the antibacterial solution. Preferably, the concentration of the silicate is from about 0.4 wt % to about 15 wt % in the antibacterial solution. More preferably, the concentration of the silicate is from about 2 wt % to about 6 wt % in the antibacterial solution. In a preferred embodiment, the concentration of the silicate is about 4 wt % in the antibacterial solution. The concentrations of silicate are calculated on the basis of the weight of anhydrous silicate and the total weight of the antibacterial solution. Either the anhydrous form or a hydrated form of silicate may be used to form the antibacterial solution, provided that the appropriate adjustment is made to compensate for the weight of any associated water of hydration.

In an extremely preferred embodiment, the antibacterial aqueous solution comprises tri-sodium phosphate (TSP) dodecahydrate ($Na_3PO_4.12H_2O$), sodium citrate, and SMS.

The antibacterial aqueous solution of the present invention can be made by dissolving the phosphate, citrate, and silicate in water. There is no specific limitation on water as a solvent for the invention. For example, taking cost into consideration, the solvent may be tap water. However, it should be understood that tap water may contain minor amounts of other components, and the antibacterial aqueous solution thus prepared is also within the scope of the present invention.

Optionally, the antibacterial aqueous solution of the present invention may further comprise a component (D), which is selected from the group consisting of carbonate, hydroxide, chloride, sulfate, ammonia, and mixture thereof. Examples of carbonate include anhydrous or hydrated sodium carbonate, anhydrous or hydrated sodium bicarbonate, anhydrous or hydrated potassium carbonate, and anhydrous or hydrated potassium bicarbonate. Examples of hydroxide include sodium hydroxide and potassium hydroxide. Examples of chloride include sodium chloride and potassium chloride. Examples of sulfate include sodium sulfate and potassium sulfate. A preferred component (D) is selected from sodium hydroxide and sodium carbonate.

In a highly preferred embodiment, the component (D) has a concentration of, based on the total weight of the antibacterial solution, from 0.05 wt % to 15 wt %, preferably from 0.2 wt % to 7 wt %, more preferably from 0.4 wt % to 2 wt %.

In the antibacterial solution, there exists an acid-base equilibrium between phosphate, citrate, silicate, optional component (D), and other minor tap water trace components. Preferably, the pH value of the final antibacterial aqueous solution is controlled to provide a range from about 11 to 14, preferably from about 12 to 13.5, more preferably from about 12.75 to 13.25.

When used in controlling bacterial contamination and/or growth in a food substance, the antibacterial aqueous solution of the present invention can be at a temperature of from about 0 to about 85° C., more preferably from about 0 to 70° C., still more preferably from about 10° C. to about 50° C. and even more preferably from about 20° C. to about 40° C.

The mechanism of controlling bacterial contamination and/or growth by the antibacterial aqueous solution of the present invention may be that, for example, the solution is able to lyse, destroy or otherwise disrupt the structure of the outer membrane of bacteria occurring in food substance. As used herein, the terminology "controlling bacterial contamination and/or growth" refers generally to reducing bacterial contamination or retarding bacterial growth, as well as both reducing bacterial contamination and retarding bacterial growth.

Optionally, the antibacterial aqueous solution of the present invention may be combined with other antibacterial treatments to improve the effectiveness of controlling bacterial contamination and/or growth below a target value, for example, physical measures, antibacterial chemicals, and antibacterial biochemicals.

Exemplary physical measures include, but are not limited to, washing carcasses with hot water, e.g., at a temperature of from about 160° F. to about 180° F.; and cleaning carcasses with steam and vacuum, and the like.

Exemplary antibacterial chemicals include, but are not limited to, chlorine; hops acid extracts or hops resins; propionibacteria metabolites; chitosan; tertiary butyl hydroquinone (TBHQ); chlorine dioxide; sterilant gases such as ethylene oxide and propylene oxide; ammonium tetraformate; acids such as lactic acid, acetic acid, propionic acid, sorbic acid, tartaric acid, benzoic acid, nitric acid, acyloxyalkenoic acid, and salt thereof; and mixture thereof.

The bitter components of the hops used in beer making, particularly the beta-acids, have now been found to be useful as bactericidal agents in food products. The most prevalent groups of bitter acids contained in hops are the alpha-acids and the beta-acids, also referred to as humulones and lupulones, respectively. Both contribute bitterness to beer, but the alpha-acids are much bitterer than the beta-acids and not desirable for use in most food products. Producers of hops extract isolate the alpha and beta acids commercially by various chromatographic methods and have developed a technique to separate the two acid fractions using liquid carbon dioxide under supercritical conditions. A by-product of the operation is a product which contains approximately 61 weight percent beta-acids, the remainder consisting essentially of hops resins. This by-product can be standardized with malto dextrin or other food grade carrier, spray dried, and used as an antibacterial food ingredient.

The alpha-acids contained in hops are commonly known as humulone, cohumulone and adhumulone, while the beta-acids contained in hops are commonly known as lupulone, colupulone and adlupulone. Chemically modified derivatives of hops acids or hops resins which have demonstrated antibacterial properties such as hexahydrocolupulone and tetrahydroisohumulone, as disclosed in U.S. Pat. No. 5,455,038, are specifically contemplated for use in association with the present invention. Also considered as specifically contemplated for use in association with the present invention is the use of any suitable salt form of the hops acids or hops resins.

Propionibacteria metabolites may be obtained by growing propionibacteria, e.g. *Propionibacterium shermanii, P. freudenreichii, P. pentosaceum, P. thoenii, P. arabinosum, P. rubrum, P. jensenii, P. peterssonii*, and related species (as identified in Malik et al., Can. J. Microbiol. 14:1185, 1968) in a milk, cheese whey, or broth medium, or other suitable nutrient mixtures. The resulting growth liquid can then be added to food substance to inhibit gram negative bacteria. The metabolites may be separated or purified or used as a mixture. Powdered or liquid natural propionibacteria metabolites can be incorporated into various food substances to render them less susceptible to spoilage by growth and/or enzymatic activity of gram negative bacteria.

Commercially available propionibacteria metabolites may be obtained from Rhodia Inc. under the MICROGARD® trademark. MICROGARD® MG 100 is a pasteurized cultured skim milk that is standardized with skim milk solids, and spray dried. MICROGARD® MG 200 is a pasteurized cultured dextrose that has been standardized with maltodextrin, and spray dried. MICROGARD® MG 250 is a condensed (frozen or liquid) version of the cultured dextrose product. Propionibacterium strains identified by number are available from the American Type Culture Collection (ATCC). The other cultures are widely available or can be obtained from Oregon State University, Corvallis, Oreg.

Any suitable antibacterial biochemical that is effective in controlling bacterial contamination and/or growth may be present in the invention. Exemplary antibacterial biochemicals against gram positive bacteria may include, but are not limited to, lantibiotics, lysozyme, pediocin, and lacticin class bacteriocins.

The term "lantibiotics" was coined by Schnell et al. (1988. Nature 333:276-278) to describe a group of bacteriocins including nisin which contain the amino acid lanthionine and other "nonprotein" amino acids. The common properties of these bacteriocins are reviewed by Kellner et al. (1988. Eur. J. Biochem 177:53-59) wherein they note that " . . . polycyclic polypeptide antibiotics possess a high content of unsaturated amino acids (dehydroalanine, dehydrobutrine) and thioether amino acids (mesolanthionine, (2S,3S,6R)-3-methyllanthionine). Furthermore, lysinoalanine, 3-hydroxyaspartic acid and S-(2-aminovinyl)-D-cystine are found in some members". Members of this group include nisin, subtilin, pep 5, epidermin, gallidermin, cinnamycin, Ro09-0198, duramycin and ancovenin. These ribosomally synthesized peptide antibiotics contain from 19 to 34 amino acids and are produced by various microbes including *Staphlococcus* species, *Bacillus* species and *Streptomyces* species. In addition to their unique composition of non-protein amino acids, they can be distinguished from other polypeptide antibiotics on the basis of their specificity. Bacteriocins in general, and the lantibiotics in particular, are characterized by a very narrow spectrum of action. Thus, only a few species of bacteria are sensitive to a particular bacteriocin at practical concentrations. This is in contrast with other broad spectrum polypeptide antibiotics, such as polymixin B1 which are active against most bacteria and the "lytic peptides" discussed by Jaynes et al., in published international application WO 89/00194, which are active against most bacteria, yeasts and even mammalian cells.

Nisin occasionally occurs as a dimer with a molecular weight of about 7000. It contains several unusual amino acids including b-methyllanthionine, dehydroalanine, and lanthionine among its total of 34 amino acids. There are five unusual thio-ether linkages in the peptide which contribute to its stability in acid solutions. Nisin is one of the most thoroughly characterized bacteriocins, and shares remarkable homology of structure and action with other lantibiotics, for example Subtilin and epidermin (Buchman et al 1988. J. Bio. Chem. 263 (31):16260-16266). Recent reviews of nisin, its physical properties and uses include "Bacteriocins of Lactic Acid Bacteria", T. R. Klaenhammer, 1988. Biochimie 70:337-349, "Nisin", A. Hurst, 1981. Avd. Appl. Microbiol. 27:85-121, and U.S. Pat. No. 4,740,593. Nisin is the collective name describing several closely related substances which exhibit similar amino acid compositions, and some limited range of antibiotic activity. This phenomenon is discussed by E. Lipinska in "Antibiotics and Antibiosis in Agriculture" (M. Woodbine, Ed.) pp. 103-130.

The use of nisin to combat *L. monocytogenes* has been reported by M. Doyle; "Effect of Environmental and Processing Conditions on *Listeria Monocytogenes*", Food Technology, 1988.42(4):169-171. This reference describes the initial inhibition of the organism's growth (for about 12 hours) and reports that *L. monocytogenes* may grow at a pH level as low as 5.0 and is resistant to alkaline pH with the ability to grow at pH 9.6.

Nisin is commercially available from Rhodia Inc. under the trademark MICROGARD® MG300, and in purified form under the trademark Novasin™. In practice, the lantibioitic is added to the food product in amounts between about 1 to about 25 ppm (by weight of solution used for treatment) of active ingredient (nisin).

Lysozyme may also be used, in collaboration with the aqueous solution of the invention, to improve the effectiveness of controlling bacterial contamination and/or growth. When lysozyme is used, it is added to the food product in amounts between about 20 to about 500 ppm (by weight of solution used for treatment), more preferably between about 50 to about 100 ppm. Lysozyme is also commercially available from Rhodia under the trademark NovaGARD™. Lysozymes (Muramidase; mucopeptide N-acetylmucamoyl-hydrolase; 1,4-β-N acetylhexosaminodase, E. C. 3.2.1.17) are mucolytic enzymes which have been isolated from various sources and are well characterized enzymes. First discovered in 1922 by W. Fleming, egg white lysozyme was among the first proteins sequenced, the first for which a three dimensional structure was suggested using x-ray crystallography and the first for which a detailed mechanism of action was proposed. Its antimicrobial activity against gram positive bacteria is well documented, for example by V. N. Procter et al in CRC Crit. Reviews in Food Science and Nutrition, 1988, 26(4):359-395. The molecular weight of egg white lysozyme is approximately 14,300 to 14,600, the isoelectric point is pH 10.5-10.7. It is composed of 129 amino acids which are interconnected by four disulfide bridges. Similar enzymes have been isolated and characterized from other sources including such diverse producers as *Escherichia coli* bacteriophage T4 and human tears. Despite slight differences (for example, the human lysozyme has 130 amino acids) the capacity for hydrolysis of acetylhexosamine polymers remains essentially the same. Accordingly, for purposes of this invention, the term lysozyme is intended to include those outer membrane degrading enzymes which have the ability to hydrolyze acetylhexosamine and related polymers.

Lysozyme is known to kill or inhibit the growth of bacteria and fungi, and is used in Europe to control the growth of the spoilage organism *Clostridium tyrobutyrucum* in cheese. It has also been proposed for use in a variety of other food preservation applications and has been reported to inhibit the growth of (and in some cases kill) *Listeria monocytogenes* (Hughey et al, 1987, Appl. Environ. Microbiol 53:2165-2170).

To improve the effectiveness of controlling bacterial contamination and/or growth, the antibacterial aqueous solution of the invention may also be used, in cooperation with lacticins, and pediococcus bacterial metabolite, specifically pediocin. Both lacticins and pediocins are compounds known to have selected activity against gram positive, but not gram negative bacteria.

In various embodiments of the present invention, the contamination and/or growth of a wide spectrum of bacteria in food substance may be controlled by the antibacterial aqueous solution, singly or in combination with other antibacterial treatment(s). The bacterial may include gram negative bacteria such as *E. Coli, salmonella*, campylobacter and the like; gram negative spoilage bacteria such as *Pseudomonus aeruginosa*, alcaligenes, and erwinia species etc; gram positive pathogens such as *Listeria monocytogenes, Staphylococcus aureus, Bacillus cereus, Clostridium botulinum, C. perfringens, Corynebacteria, Diplococci, Mycobacteria, Streptococci, Streptomyces*, and the like. Examples of *salmonellae* include *Salmonella typhimurium, S. choleraesuis* and *S. enteriditis*; Examples of *E. coli* include *E. coli* ATCC 25922, *E. coli* ATCC 8739 and *E. coli* O 157:H7 ATCC 43895 etc.

The bacterial level in the food substance may be measured by, for example, a standard aerobic plate count on colony forming units (CFU) in a normalized sample. For example, *E. coli* counts may be determined by *E. coli/coliform* count plate testing (Petrifilm™ (3M)) according to AOAC Official Method 991.14. *Salmonella* counts may be determined by subjecting samples with three broth enrichment steps to colorimetric deoxyribonucleic acid hybridization testing (GENE-TRAK™ (Neogen Corporation)) according to AOAC Official Method 990.13. Presumptive positive results may be, in general, confirmed according to FDA-BAM ($8^{th}$ Edition Revision A, 1998). Results are reported as the percentage of positive results, calculated as: ((number of positive results in the test series/total number of samples in the test series)×100).

The antibacterial aqueous solution of the present invention may be used to treat a variety of food substances, for example, edible fruits and vegetables, edible animals such as birds, fish, crustaceans, shellfish, and mammals etc. Examples of edible fruits and vegetables include, but are not limited to, lettuce, tomatoes, cucumbers, carrots, spinach, kale, chard, cabbage, broccoli, cauliflower, squash, beans, peppers, apples, oranges, pears, melons, peaches, grapes, plums, and cherries. Exemplary birds include chickens, turkeys, geese, capon, game hens, pigeon, ducks, guinea fowl, pheasants, quail, and partridges. Exemplary fish include, catfish, trout, salmon, flounder, tuna, swordfish, and shark. Exemplary crustaceans include crayfish, shrimp, prawns, crabs, and lobsters. Exemplary shellfish include clams, scallops, oysters, and mussels. Exemplary mammals include cattle, pigs, sheep, lambs, and goats.

Additives suitable for the food substance are well-known to a skilled person in the art, for example, natural or synthetic seasonings, essential oils, flavors, dyes or colorants, vitamins, minerals, nutrients, enzymes, binding agents such as guar gum and xanthan gum, and the like. In preferred embodiments, guar gum is used to aid in the binding of antimicrobial agent(s) to the food surface being treated.

In a preferred embodiment of the present invention, the antibacterial aqueous solution is used to treat eviscerated animal carcass, in which the internal organs of the animal are removed. An eviscerated carcass typically comprises bones, skeletal muscle and associated fascia. In a preferred embodiment, the skin is not removed from the eviscerated carcass of a fish or a bird prior to treatment with the antibacterial aqueous solution of the present invention. In another preferred embodiment, the skin is removed from the eviscerated carcass of a mammal priorto treatment with the antibacterial aqueous solution of the present invention. In various embodiments, the method of the present invention is suitable as the primary step of a carcass processing line for reducing bacterial contamination of the carcass below a target value.

For example, an animal carcass may contact with the antibacterial aqueous solution after slaughter, either prior to, during or after chilling, by dipping the carcass in the antibacterial aqueous solution or by spraying the antibacterial aqueous solution on the carcass. In a preferred embodiment, the animal carcass is contacted with the antibacterial aqueous solution by spraying the solution under a gage pressure of greater than 2 pounds per square inch above atmospheric pressure (psig), more preferably from 2 to 400 psig, onto all accessible surfaces of the carcass. In another preferred embodiment, a bird carcass may be contacted with the antibacterial aqueous solution by spraying the solution onto the carcass at a pressure of from 3 to 40 psig. In still another preferred embodiment, a mammalian carcass is contacted with the antibacterial aqueous solution by spraying the solution onto the carcass at a pressure of from 20 to 150 psig.

An animal carcass may be contacted with the antibacterial aqueous solution for greater than or equal to about 1 second to about 5 minutes, more preferably from about 5 seconds to about 2 minutes, and even more preferably from about 15 seconds to about 1 minute. The preferred contact times refer to the duration of the active application process, for example, dipping or spraying, used to contact the antibacterial aqueous solution with the carcass. For example, an animal carcass may be submerged in a container of the antibacterial aqueous solution for 15 seconds, withdrawn from the solution, allowed to drip for 30 seconds, and placed in a plastic bag. Once applied, the antibacterial aqueous solution can be immediately rinsed off from the carcass or, alternatively, allowed to remain on the carcass. Animal carcasses that have been treated according to the present invention can, immediately after such treatment, be processed according to normal carcass process conditions, such as draining or chilling. Optionally, the antibacterial aqueous solution residue may be rinsed from the carcass priorto further processing.

A carcass may be rinsed by adding an appropriate amount of acidic buffer such as Butterfield's buffer to the plastic bag containing the carcass and then shaking the carcass in bag of buffer, during which any residual basic antibacterial solution may be neutralized. Rinse solutions may then be removed from the bag and chilled by placing containers of the carcass on water ice in shipping containers.

The antibacterial treatment according to the present invention allows simple and economical washing of food animal carcasses to reduce bacterial contamination of the carcass and/or retard bacterial growth on the carcass, without substantial detriment to the organoleptic properties of the carcass and without generating a waste stream that contains a higher amount of phosphates. Organoleptic properties include the sensory properties such as the appearance, texture, taste, and smell etc.

As another important merit, the present invention provides a method of prohibiting the formation of, and/or facilitating the removing of, silicate aggregation on metal article, comprising using the antibacterial aqueous solution with the metal article. In industrial food processing facilities, the silicate aggregation is known as unpleasant "scale", white spot, stain, sticky gummy residue, and the like. The metal article may be any metal tools or equipment in a food processing facility such as shackle, shank of shackles, drip pan, cabinet, floor and companion equipments etc.

Without being bound by theory, it is believed that the silicate aggregation is formed by silicate denaturing, when the silicate is, for example, applied to food substance such as poultry carcass in an industrial setting on a continuous recycle of solution reconstituted to its original strength. All of the accumulated by-products from the application remain in the solution at an equilibrium concentration governed by the natural process purge. The denaturing of the silicate solution such as sodium meta-silicate (SMS) causes a precipitation to occur which coats the surface of metal article and which contains silicates. In time, for example one day's operation, the silicate changes to a silica or poly silica, which bonds very tenaciously to a metal surface such as iron.

Common detergents may be utilized to remove the silicate aggregation. Exemplary detergents include the family of Mirataine compounds available from Rhodia and the compounds available from Unisan.

Advantageously, the present invention is believed to provide adequate antimicrobial activity with limited scale formation and/or more easily scale removal.

Advantageously, it is envisioned that the addition of a citrate compound to the phosphate and silicate compounds may provide improved antimicrobial activity.

In a preferred embodiment, the antibacterial aqueous solution is recovered and recycled. Preferably, the recovered solution is filtered to remove solids prior to recycling. Preferably, the respective amounts of the one or more components of the antibacterial aqueous solution are monitored and desirable antibacterial aqueous solution is rebuilt by adding appropriate amounts of phosphate, citrate, silicate, water, carbonate, and/or hydroxide into the solution.

EXAMPLES

The following examples are provided to help explain the invention. They are not intended to limit the scope of the invention as defined by the appended claims.

Experiments were performed on both a bench scale and at the pilot plant level. In each case, an antimicrobial solution on 4% sodium metasilicate (INEOS), 1% tri-sodium phosphate dodeca (AvGard), and 1% sodium citrate (Danisco) was prepared in water. In the bench scale experiments, a chicken carcass was immersed in the solution for periods between 4 and 16 hours to obtain a broth. The obtained broth was then splashed on the surface of 2×5 inch stainless steel coupons for periods between 16 and 192 hours. Coupons were evaluated on repetitive basis such as multiple day exposures, and usually inspected on a daily basis. Splashing was achieved by agitating the broth. More particularly, broth was splashed using a peristaltic pump dispersing the broth onto the rotating surface of a propeller adjacent the coupons. Resultant coupons were removed and cleaned, either immediately or subsequent to drying. Cleaning was performed using Mirataine JCHA, Mirataine H2 CHA, or Mirataine CBS. The evaluated coupons were assessed based on a visual inspection and rated according to the visible quantity of scale deposits. The results showed excellent scale inihibition/removal using the above-described antimicrobial solution with ratings between 6-10 on a 10 point scale, while comparative teaching using alternative broth solutions demonstrated relatively lower scale inhibition.

To conduct the pilot plant experiments, the above-identified solution was prepared using 40 lbs. SMS, 10 lbs. TSP and 10 lbs. sodium citrate in 940 lbs. water. The pilot plant was run for 8 hour cycles using the subject solution in accord with typical carcass treatment procedures. Following the cycle, drip pans and shackles were cleaned and visually evaluated for scale build-up. Equipment was cleaned alternatively both before and after drying. Cleaning was performed using one of water, 1% Mirataine in 5% NaOH, or 1.5% Mirataine CBS in 5% NaOH. The process was repeated over a period of several weeks, being repeated between 1 and 3 times per week. The experimentation demonstrated an ability to remove scale residue from shackles with water wash and an ability to remove scale residue from drip pans with waterwash and improved scale removal with Mirataine cleanser. The ability to achieve these results was demonstrated over the several weeks of evaluation.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A food cleaner consisting of:
   a. a phosphate having the formula of (I) in a concentration of from 0.1% to 4% based on the total weight of the solution,
   b. a citrate having the formula of (II) in a concentration of from 0.1% to 4% based on the total weight of the solution, and
   c. a silicate having the formula $[(M_7)_2O].(SiO_2)_m.(H_2O)_z$ in a concentration of from 0.4% to 15% based on the total weight of the solution,

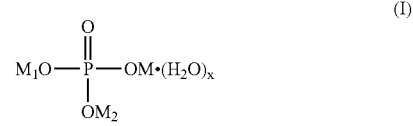

(I)

-continued

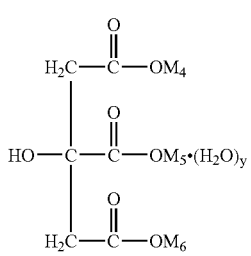

in which $M_1$, $M_2$, $M_3$, $M_4$, $M_5$, $M_6$, and $M_7$ are independently of each other selected from the group consisting of Hydrogen, Sodium, and Potassium; x, y, and z are independently of each other any number between 0 to 12; and m is any number between 1 to 6, and optionally:
d. a further component which is selected from the group consisting of carbonate, hydroxide, chloride, sulfate, ammonia, and mixtures thereof; and/or
e. an antibacterial chemical selected from the group consisting of chlorine, hops acid extracts or hops resins, propionibacteria metabolites, chitosan, tertiary butyl hyroquinone (TBHQ), chlorine dioxide, sterilant gases selected from the group consisting of ethylene oxide and propylene oxide, ammonium tetraformate, acids selected from the group consisting of lactic acid, acetic acid, propionic acid, sorbic acid, tartaric acid, benzoic acid, nitric acid, acyloxyalkenoic acid, and salt thereof, and mixtures thereof; and/or
f. an antibacterial food ingredient; and/or
g. a solvent.

2. The food cleaner of claim 1, in which $M_1$, $M_2$, and $M_3$ are all sodium.

3. The food cleaner of claim 1, in which x=12.

4. The food cleaner of claim 1, in which the phosphate is selected from the group consisting of tn-sodium phosphate dodecahydrate ($Na_3PO_4.12H_2O$), tri-sodium phosphate hexahydrate, and mixture thereof.

5. The food cleaner of claim 1, in which the phosphate has a concentration of from 0.5% to 2% based on the total weight of the solution.

6. The food cleaner of claim 1, in which $M_4$, $M_5$, and $M_6$ are all sodium.

7. The food cleaner of claim 1, in which the citrate has a concentration of from 0.5% to 2% based on the total weight of the solution.

8. The food cleaner of claim 1, in which the silicate is selected from the group consisting of sodium disilicate, sodium metasilicate, potassium disilicate, potassium metasilicate, and mixture thereof.

9. The food cleaner of claim 1, in which m=1.

10. The food cleaner of claim 1, in which z is in the range from 0 to 9.

11. The food cleaner of claim 1, in which z is 0, 5, 6, or 9.

12. The food cleaner of claim 1, in which the silicate is selected from the group consisting of anhydrous sodium metasilicate, anhydrous potassium metasilicate, sodium metasilicate pentahydrate, potassium metasilicate pentahydrate, sodium metasilicate hexahydrate, potassium metasilicate hexahydrate, sodium metasilicate nonahydrate, potassium metasilicate nonahydrate, and mixture thereof.

13. The food cleaner of claim 1, in which the silicate comprises a crystalline $[Na_2O].(SiO_2)_m.(H_2O)_z$, wherein m is in the range of 0.5 to 3.5; and the water content of the silicate is in the range of 0% to 55 wt %.

14. The food cleaner of claim 1, in which the silicate has a concentration of about 2% to 6% based on the total weight of the solution.

15. The food cleaner of claim 1, comprising tri-sodium phosphate (TSP) dodecahydrate ($Na_3PO_4.12H_2O$), sodium citrate, and sodium meta-silicate (SMS).

16. The food cleaner of claim 1, in which the solvent of the solution is tap water.

17. The food cleaner of claim 1, in which a component (D) is selected from the group consisting of anhydrous or hydrated sodium carbonate, anhydrous or hydrated sodium bicarbonate, anhydrous or hydrated potassium carbonate, anhydrous or hydrated potassium bicarbonate, sodium hydroxide, potassium hydroxide, sodium chloride, potassium chloride, sodium sulfate, potassium sulfate, and mixture thereof.

18. The food cleaner of claim 17, in which the component (D) is selected from the group consisting of sodium hydroxide, sodium carbonate, and mixture thereof.

19. The food cleaner of claim 1, in which the component (D) has a concentration of from 0.2% to 7% based on the total weight of the solution.

20. The food cleaner of claim 19, in which the component (D) has a concentration of from 0.4% to 2% based on the total weight of the solution.

21. The food cleaner of claim 1, which has a pH value of from 11 to 14.

22. The food cleaner of claim 21, which has a pH value of from 12 to 13.5.

23. The food cleaner of claim 22, which has a pH value of from 12.75 to 13.25.

24. A method of controlling bacterial contamination and/or growth in food substance, comprising contacting the food substance with an antibacterial solution consisting of:
a. a phosphate having the formula of (I) in a concentration of from 0.1% to 4% based on the total weight of the solution,
b. a citrate having the formula of (II) in a concentration of from 0.1% to 4% based on the total weight of the solution, and
c. a silicate having the formula $[(M_7)_2O].(SiO_2)_m.(H_2O)_z$ in a concentration of from 0.4% to 15% based on the total weight of the solution,

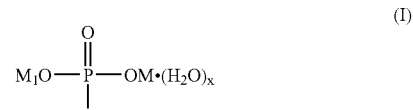

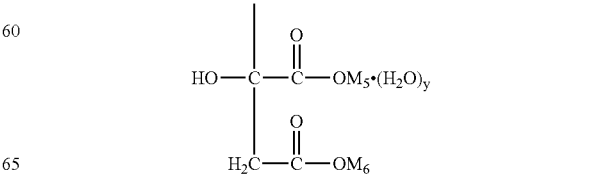

in which $M_1$, $M_2$, $M_3$, $M_4$, $M_5$, $M_6$, and $M_7$ are independently of each other selected from the group consisting of Hydrogen, Sodium, and Potassium; x, y, and z are independently of each other any number between 0 to 12; and m is any number between 1 to 6, and optionally:

d. a further component which is selected from the group consisting of carbonate, hydroxide, chloride, sulfate, ammonia, and mixtures thereof; and/or e. an antibacterial chemical selected from the group consisting of chlorine, hops acid extracts or hops resins, propionibacteria metabolites, chitosan, tertiary butyl hyroquinone (TBHQ), chlorine dioxide, sterilant gases selected from the group consisting of ethylene oxide and propylene oxide, ammonium tetraformate, acids selected from the group consisting of lactic acid, acetic acid, propionic acid, sorbic acid, tartaric acid, benzoic acid, nitric acid, acyloxyalkenoic acid, and salt thereof, and mixtures thereof; and/or f. an antibacterial food ingredient; and/or (G) a solvent.

25. The method of claim 24, further comprising treating the food substance with an antibacterial chemical which is selected from the group consisting of chlorine;

hops acid extracts or hops resins; propionibacteria metabolites; chitosan; tertiary butyl hydroquinone (TBHQ); chlorine dioxide; sterilant gases selected from the group consisting of ethylene oxide and propylene oxide; ammonium tetraformate; acids selected from the group consisting of lactic acid, acetic acid, propionic acid, sorbic acid, tartaric acid, benzoic acid, nitric acid, acyloxyalkenoic acid, and salt thereof; and mixture thereof.

26. The method of claim 25, in which the propionibacteria metabolites are obtained by growing a propionibacteria strain selected from the group consisting of *Propionibacterium shermanii, P. freudenreichii, P. pentosaceum, P. thoenii, P. arabinosum, P. rubrum, P. jensenii,* and *P. peterssonii.*

27. The method of claim 24, further comprising treating the food substance with an antibacterial biochemical.

28. The method of claim 27, in which the antibacterial biochemical is selected from the group consisting of lantibiotics, lysozyme, pediocin, lacticin, and mixture thereof.

29. The method of claim 28, in which the lantibiotics is selected from the group consisting of nisin, subtilin, pep 5, epidermin, gallidermin, cinnamycin, Ro09-0198, duramycin, ancovenin, and mixture thereof.

30. The method of claim 24, in which the bacterium is selected from the group consisting of gram negative bacteria selected from the group consisting of *E. Coli, salmonella, and campylobacter*; gram negative spoilage bacteria selected from the group consisting of *Pseudomonus aeruginosa, alcaligenes,* and *erwinia* species; gram positive pathogens selected from the group consisting of *Listeria monocyto genes, Staphylococcus aureus, Bacillus cereus, Clostridium botulinum, C. perfringens, Corynebacteria, Diplococci, Mycobacteria, Streptococci,* and *Streptomyces.*

31. The method of claim 24, in which the food substance is an edible fruit, vegetable, or animal.

32. The method of claim 31, in which the fruit or vegetable is selected from the group consisting of lettuce, tomato, cucumber, carrot, spinach, kale, chard, cabbage, broccoli, cauliflower, squash, bean, pepper, apple, orange, pear, melon, peach, grape, plum, cherry, and mixture thereof.

33. The method of claim 31, in which the animal is selected from the group consisting of chicken, turkey, geese, capon, game hen, pigeon, ducks, guinea fowl, pheasants, quail, partridge, catfish, trout, salmon, flounder, tuna, swordfish, shark, crayfish, shrimp, prawn, crab, lobster, clam, scallop, oyster, mussel, cattle, pig, sheep, lamb, goat, and mixture thereof.

34. The method of claim 31, in which the food substance is a eviscerated animal carcass.

35. The method of claim 24, further comprising adding an additive to the food substance.

36. The method of claim 35, in which the additive is selected from the group consisting of natural or synthetic seasoning, essential oil, flavor, dye or colorant, vitamin, mineral, nutrient, enzymes, binding agents such as guar gum and xanthan gum, and mixture thereof.

37. A method of prohibiting the formation of, and/or facilitating the removal of, scale aggregation on metal article, comprising using the antibacterial aqueous_solution as defined in claim 1.

38. The method of claim 37, further comprising cleaning the scale with a detergent.

39. The method of claim 38, in which the metal article is selected from a shackle, shank of shackles, drip pan, cabinet, floor and companion equipment.

40. The method of claim 24, further comprising recovering and recycling the antibacterial aqueous solution.

41. The method of claim 31, in which the animal is selected from the group consisting of bird, fish, crustacean, mammal, and mixture thereof.

* * * * *